United States Patent
Formanek et al.

(10) Patent No.: US 11,504,484 B2
(45) Date of Patent: Nov. 22, 2022

(54) INLINE MICROGRAVITY AIR TRAP DEVICE AND AN INTRAVENOUS ASSEMBLY INCORPORATING AN INLINE MICROGRAVITY AIR TRAP DEVICE

(71) Applicants: Arthur Formanek, Cambridge, MA (US); Mark Ottensmeyer, Watertown, MA (US); Tovy Kamine, Portsmouth, NH (US)

(72) Inventors: Arthur Formanek, Cambridge, MA (US); Mark Ottensmeyer, Watertown, MA (US); Tovy Kamine, Portsmouth, NH (US)

(73) Assignee: Arthur Formanek, Cambridge, MA (US)

(*) Notice: Subject to any disclaimer, the term of this patent is extended or adjusted under 35 U.S.C. 154(b) by 221 days.

(21) Appl. No.: 16/924,674

(22) Filed: Jul. 9, 2020

(65) Prior Publication Data
US 2020/0338278 A1   Oct. 29, 2020

Related U.S. Application Data

(63) Continuation-in-part of application No. 16/576,448, filed on Sep. 19, 2019, now Pat. No. 10,737,018.

(60) Provisional application No. 62/733,305, filed on Sep. 19, 2018.

(51) Int. Cl.
*A61M 5/38* (2006.01)
*A61M 39/10* (2006.01)
*A61M 5/142* (2006.01)

(52) U.S. Cl.
CPC ............ *A61M 5/385* (2013.01); *A61M 5/142* (2013.01); *A61M 39/10* (2013.01)

(58) Field of Classification Search
None
See application file for complete search history.

(56) References Cited

U.S. PATENT DOCUMENTS

| 3,650,093 | A | * | 3/1972 | Rosenberg | .......... | A61M 1/0005 96/6 |
| 3,827,562 | A | * | 8/1974 | Esmond | .............. | A61M 1/3627 210/304 |

(Continued)

FOREIGN PATENT DOCUMENTS

WO   2009/132816   5/2009

*Primary Examiner* — Christopher P Jones
*Assistant Examiner* — Phillip Y Shao
(74) *Attorney, Agent, or Firm* — Caldwell Intellectual Property Law

(57) ABSTRACT

An inline microgravity air trap device includes an elongate air trap chamber, the air trap chamber having a blind end, an opposite air outlet end containing a gas egress opening, a fluid inlet port connecting to a pressurized fluid supply, a fluid outlet port connecting the air trap chamber to a fluid delivery destination, a filter forming a tube having an interior, a first end at the blind end of the air trap chamber and a second end at the gas egress opening, and a structural insert in the interior of the tube, having a first insert end located at the blind end, and a second insert end located the air outlet end, where the chamber is formed to direct fluid from the pressurized fluid supply to accelerate centrifugally around the filter, forcing gas contained in the fluid to pass through the filter into the interior of the tube.

20 Claims, 9 Drawing Sheets

(56) References Cited

U.S. PATENT DOCUMENTS

| | | | | |
|---|---|---|---|---|
| 4,345,919 | A * | 8/1982 | Wilkinson | B01D 19/0031 210/436 |
| 4,490,254 | A * | 12/1984 | Gordon | A61M 1/3627 210/247 |
| 4,690,762 | A * | 9/1987 | Katsura | B01D 19/0031 210/436 |
| RE32,711 | E * | 7/1988 | Dickens | B01D 19/0057 210/304 |
| 4,919,802 | A * | 4/1990 | Katsura | A61M 1/3627 422/44 |
| 5,540,841 | A * | 7/1996 | Gsell | A61M 1/3633 210/195.1 |
| 5,632,894 | A * | 5/1997 | White | B01D 29/21 210/436 |
| 5,824,212 | A | 10/1998 | Brockhoff | |
| 6,053,967 | A | 4/2000 | Heilmann et al. | |
| 6,267,926 | B1 * | 7/2001 | Reed | A61M 1/1698 210/314 |
| 6,730,267 | B2 * | 5/2004 | Stringer | F04D 9/006 422/45 |
| 6,827,862 | B1 * | 12/2004 | Brockhoff | A61M 1/3627 210/188 |
| 7,488,448 | B2 * | 2/2009 | Wieting | A61M 1/3627 422/44 |
| 7,998,250 | B2 * | 8/2011 | Pondelick | B01D 45/12 4/DIG. 19 |
| 7,998,251 | B2 * | 8/2011 | Pondelick | B01D 45/16 95/258 |
| 8,424,685 | B2 * | 4/2013 | Smit | A61M 1/0056 210/445 |
| 8,801,684 | B2 * | 8/2014 | Walti | A61M 1/008 604/313 |
| 9,320,867 | B2 * | 4/2016 | Yeomans | A61M 16/085 |
| 10,420,867 | B2 * | 9/2019 | Minskoff | A61M 1/0056 |
| 10,500,349 | B2 * | 12/2019 | Shivkumar | B01D 19/0031 |
| 2005/0261618 | A1 * | 11/2005 | Gershowitz | A61M 1/3627 604/4.01 |
| 2006/0029514 | A1 * | 2/2006 | Lindsay | B01D 19/0031 422/44 |
| 2006/0084836 | A1 * | 4/2006 | Hubbard | A61M 1/3627 600/16 |
| 2009/0199708 | A1 | 8/2009 | Milo et al. | |
| 2009/0249955 | A1 * | 10/2009 | Bodner | B01D 19/0005 95/250 |
| 2011/0245750 | A1 * | 10/2011 | Lynch | A61M 1/3627 604/5.01 |

* cited by examiner

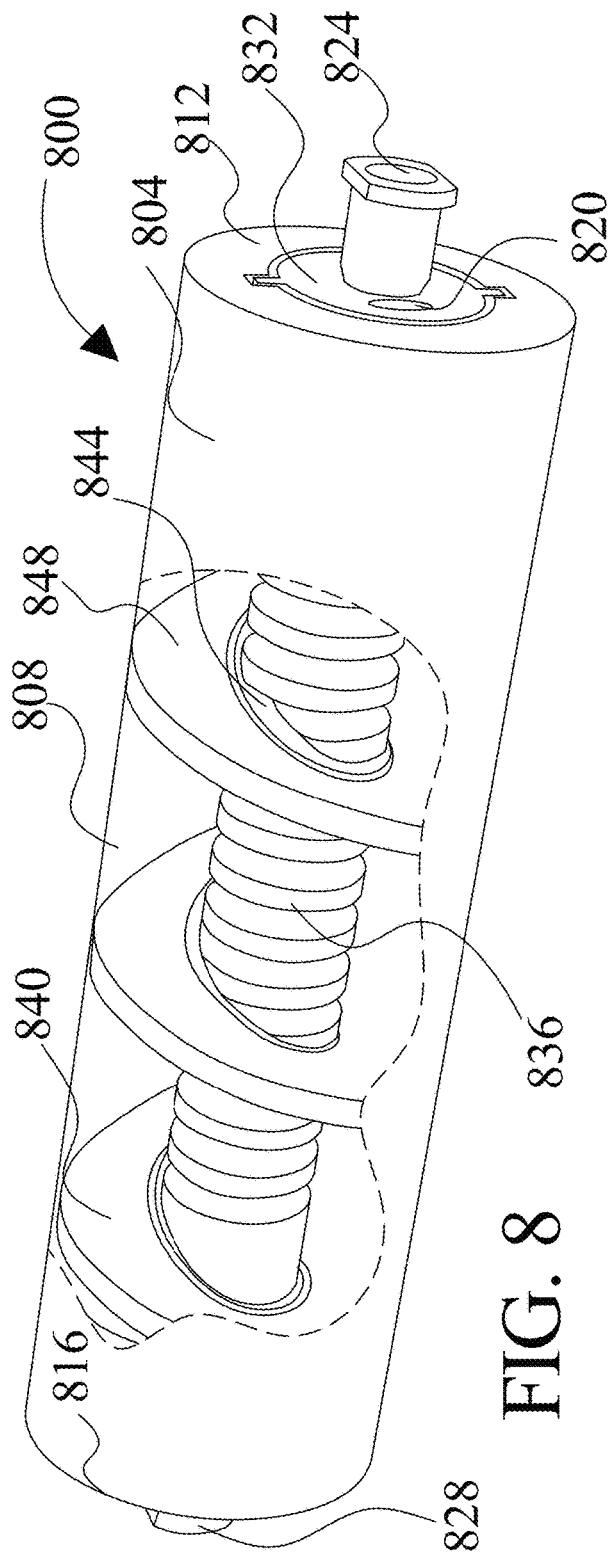
FIG. 8
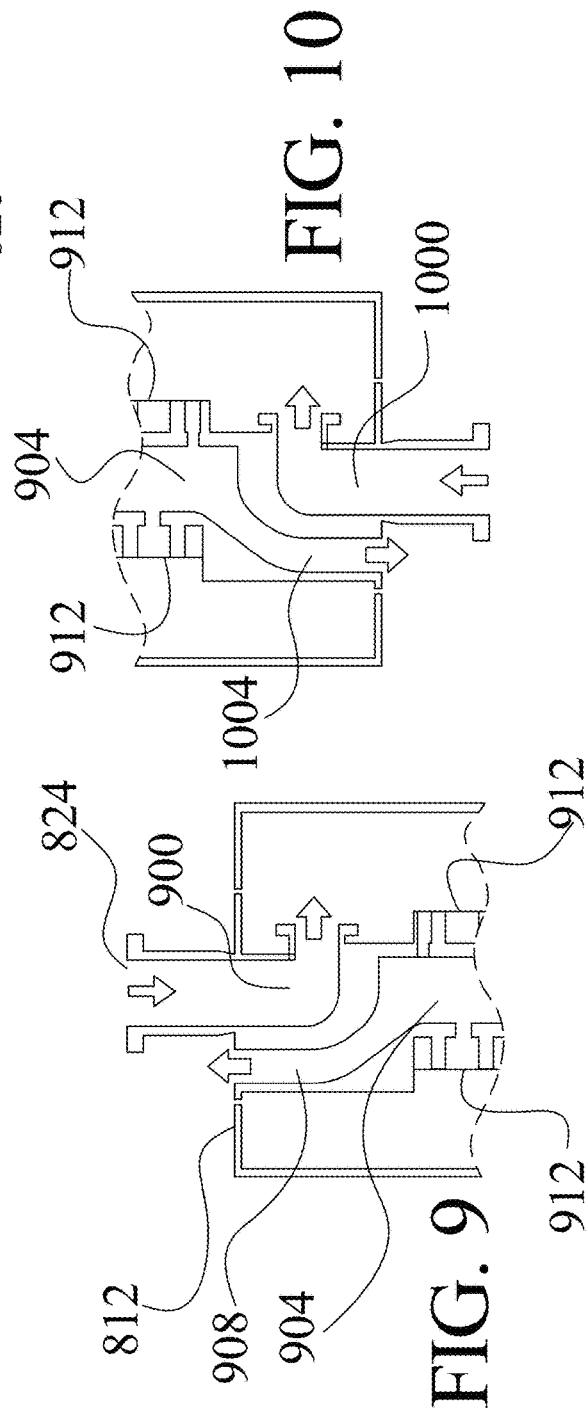
FIG. 9
FIG. 10

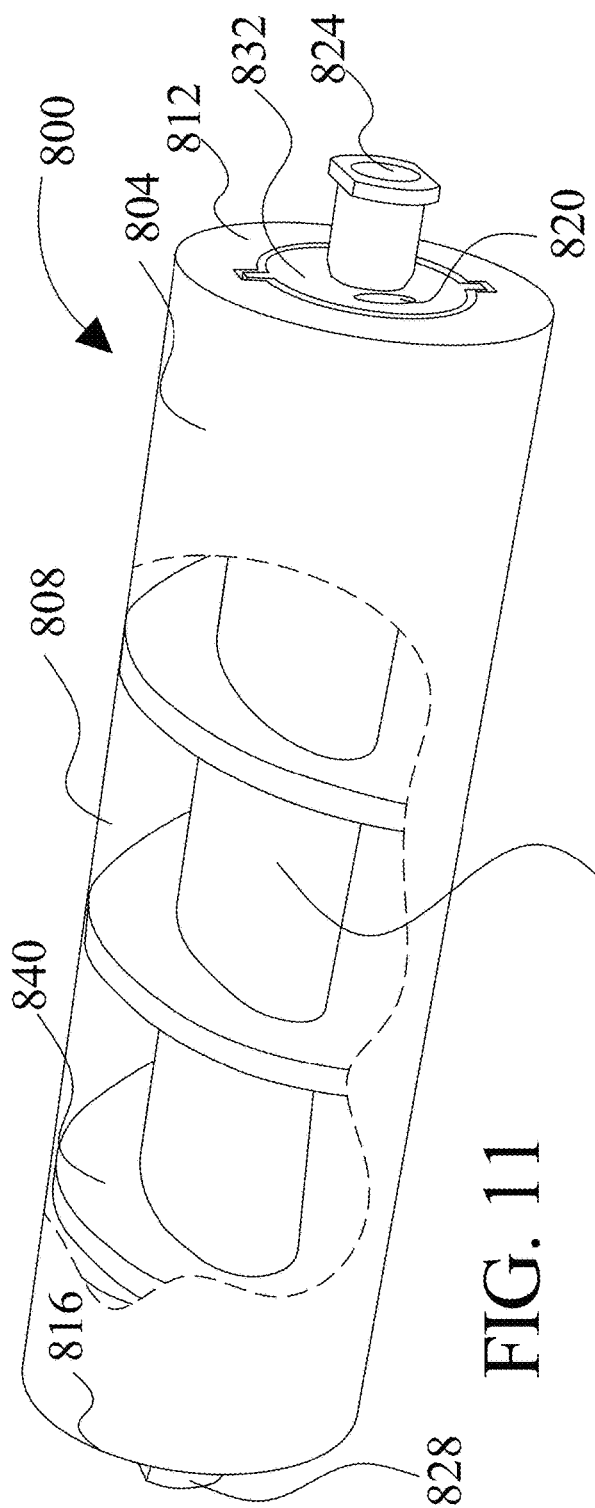
FIG. 11
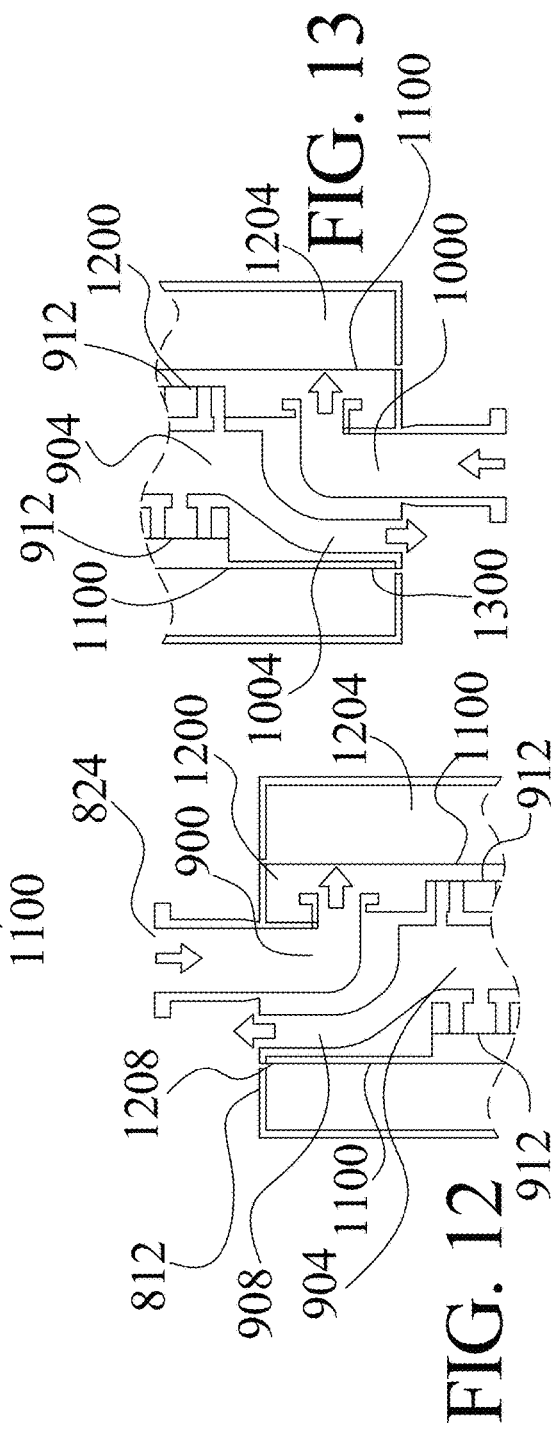
FIG. 12
FIG. 13

INLINE MICROGRAVITY AIR TRAP DEVICE AND AN INTRAVENOUS ASSEMBLY INCORPORATING AN INLINE MICROGRAVITY AIR TRAP DEVICE

CROSS-REFERENCE TO RELATED APPLICATIONS

This application is a continuation-in-part of U.S. Nonprovisional application Ser. No. 16/576,448, filed on Sep. 19, 2019, and entitled "INLINE MICROGRAVITY AIR TRAP DEVICE AND AN INTRAVENOUS ASSEMBLY INCORPORATING AN INLINE MICROGRAVITY AIR TRAP DEVICE," which claims the benefit of priority of U.S. Provisional Patent Application Ser. No. 62/733,305, filed on Sep. 19, 2018, and titled "Microgravity Air Trap." Each of U.S. Nonprovisional application Ser. No. 16/576, 448 and U.S. Provisional Patent Application Ser. No. 62/733,305 is incorporated by reference herein in its entirety.

FIELD OF THE INVENTION

The present invention generally relates to the field of medical devices. In particular, the present invention is directed to an inline microgravity air trap device and an intravenous assembly incorporating an inline microgravity air trap device.

BACKGROUND

Exclusion of air bubbles from fluids delivered in intravenous (IV) fluid delivery systems typically relies on gravity, and resulting buoyancy behavior of air, to aid in the exclusion of air bubbles. However, gravity is not available to separate fluids from gases during spaceflight. This fundamental fact of physics limits the use of certain medical equipment and procedures like anesthetic vaporizers and IV fluid delivery in microgravity. While a pressure bag can be utilized to allow the delivery of fluid, it does not solve the problem of an excessive amount of air in the IV tubing to be dispensed to the patient. Moreover, terrestrial air filters typically available for IV fluids are not designed to handle the large amount of air that may be delivered in microgravity.

SUMMARY OF THE DISCLOSURE

In an aspect, an inline microgravity air trap device, the device comprising includes an elongate air trap chamber, the air trap chamber having a first end, an opposite second end, and a longitudinal axis running from the first end to the second end, at least a gas egress opening connected to at least one of the first end and the second end, a filter, the filter forming a filter tube having an interior containing the longitudinal axis, the filter tube having a first tube end at the first end and a second tube end at the second end, a structural insert in the interior of the tube, the structural insert having a first insert end located at the first tube end and the blind end, and a second insert end located at the second tube end and the air outlet end, wherein the structural insert further includes a fluid inlet port located at the first insert end and connecting the air trap chamber to a pressurized fluid supply and a fluid outlet port located at the second insert end and connecting the air trap chamber to a fluid delivery destination, and a helical baffle running from the first end to the second end. The Helical baffle is formed to direct fluid from the pressurized fluid supply to accelerate centrifugally around the filter, forcing gas contained in the fluid to pass through the filter into the interior of the tube.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 8 is a schematic diagram illustrating an exemplary embodiment of a microgravity air trap device;

FIG. 9 is a schematic diagram illustrating an exemplary embodiment of a detail of a microgravity air trap device;

FIG. 10 is a schematic diagram illustrating an exemplary embodiment of a detail of a microgravity air trap device;

FIG. 11 is a schematic diagram illustrating an exemplary embodiment of a microgravity air trap device;

FIG. 12 is a schematic diagram illustrating an exemplary embodiment of a detail of a microgravity air trap device;

FIG. 13 is a schematic diagram illustrating an exemplary embodiment of a detail of a microgravity air trap device.

Figure 1:
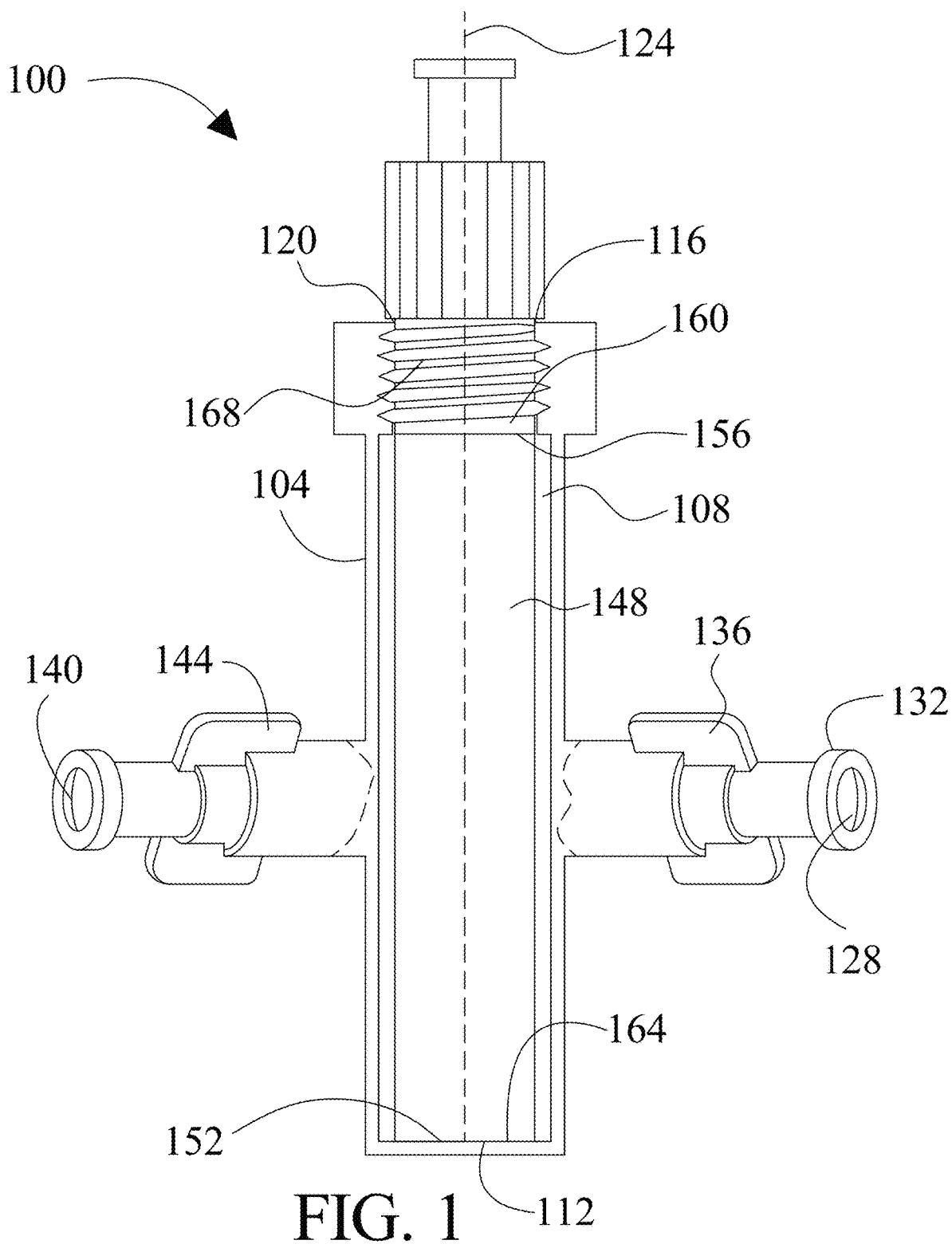
FIG. 1 is a schematic diagram illustrating an exemplary embodiment of a microgravity air trap device.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments of the disclosed microgravity air trap device allow the successful administration of IV fluid and medication during spaceflight while accounting for the unique nature of microgravity fluid dynamics. In an embodiment, a pressure source may force liquid containing at least an air bubble through a tube to a chamber so that the liquid swirls around the chamber. Resulting centrifugal force drives the fluid towards the outside of the curved chamber, causing relatively buoyant air bubbles to "float" to the middle, where they may pass through a filter into a central tube that allows air to evacuate; the filter may extend the length of the chamber, which may enable exclusion of large quantities of gas. For purposes herein, "centrifugal force"

refers to the "fictional" force, and/or force experienced by objects in frames of reference wherein objects are moving in rotational paths with some angular velocity, urging objects in an outward radial direction with respect to rotational and/or curved paths; "centrifugal acceleration," as used herein is the acceleration and/or apparent acceleration in an outward radial direction attendant to the centrifugal force. "Centripetal force," as used herein, is a force and/or force component urging objects in an inward radial direction to impose a circular path on the motion of such objects, such as the force imposed by gravity on an object in orbit, a force imposed by a string on a tethered object being whirled around a fixed point, or the like; "centripetal acceleration" is the acceleration attendant to centripetal force. Persons skilled in the art, upon reading the entirety of this disclosure, will be aware of the ways in which centrifugal force, centripetal force, centrifugal acceleration, and/or centripetal acceleration may be used to describe locally experienced accelerations in rotational frames of reference. Liquid may be output through another tube and may then proceed into a vein in which it is injected. To facilitate transport, embodiments of the device may have some components manufactured on Earth, while others may be additively manufactured with raw materials and facilities already in orbit. In addition, the device may be used terrestrially in situations in which it would be impractical to set up an air trap that must remain in a particular orientation, such as an upright orientation, relative to gravity to function effectively. Although embodiments disclosed herein are useful for microgravity environments, such embodiments may be useful in many applications where a filter is needed to remove large quantities of air or a particular orientation with respect to a direction of gravitational force is not reliably available, such as under field conditions where a patient may be carried, transported by stretcher, in moving vehicles, or the like.

Various embodiments of an inline microgravity air trap as described in this disclosure may be incorporated in IV delivery assemblies, which may, as a non-limiting example, be used to administer IV therapy. As used herein, IV therapy is a therapy involving delivery of fluids directly into blood vessels such as veins and/or arteries; IV therapy may be used to administer injections using a syringe at high pressure to deliver boluses of medication, nutrients, and/or fluids, and/or delivery of infusions, which administer medication, fluids, and/or nutrients gradually over more extended periods of time. Infusion delivery is often referred to as a "drip" because the infusion is often delivered by the effect of gravity on a fluid reservoir raised a certain distance above a patient or otherwise given a certain degree of hydrostatic head.

In spaceflight, many assumptions that permit IV therapy to work effectively are abrogated. Most spaceflight currently involves choices of various elliptical and hyperbolic orbits, either around or between celestial bodies to move efficiently in planetary or other gravity fields; as orbits are effectively free-fall paths with respect to such gravity fields, objects in orbit experience a reference frame including little or no mutual acceleration. As a result, there is no apparent effect of gravity or other acceleration except when imposed by rotation or thrust, and objects tend to "float" relative to one another. This situation, where gravity and other acceleration effects have little or no apparent power over a local environment, is referred to herein as "microgravity," and is sometimes popularly termed "zero gravity" or a "zero-gravity" environment. Among the many consequences of this environment is the negation of most familiar effects of buoyancy: it is no longer the case that a material low in density, such as a gas, intermixed in a material of relatively high density, such as a liquid, will be urged out of suspension by the effects of buoyancy and gravity, and "float to the top" of the denser material. This may result in fluid such as saline fluid bags used in IV delivery systems being intermixed with bubbles, forming a foam-like consistency; as a result, when fluid is forced through IV tubing under pressure, a far larger amount of air is intermixed with the fluid. Further exacerbating this issue, initial air-exclusion devices commonly used for infusions, such as drip chambers, rely on gravity and relative buoyancy as well, and thus are ineffective in microgravity environments.

Presence of air bubbles in fluids introduced via IV can have severe health consequences, including air embolisms, which occur where air bubbles occlude blood vessels, particularly capillaries, where the size of potentially affected vessels may depend on the size of bubbles. An air bubble of less than a certain volume, such as without limitation 30 microliters may dissolve into the circulation harmlessly. However, a large bubble, if delivered all at once, can cause life-threatening damage, for instance by blocking one or more vessels in the brain and leading to ischemic damage, or in the case of extremely large bubbles, for instance of 3-8 milliliters per kilogram of bodyweight, cardiac arrest. Arteries represent a higher risk of bubble-related health effects, as venous blood may pass through the lungs prior to exposure to narrowing vessels supplying other organs; air bubbles can leave the bloodstream through the lungs. For this reason, the higher quantity of air that is likely to be present in IV lines and to bypass traditional air exclusion systems represents a significant threat to health, and a barrier to an effective medical treatment process that is used extensively in terrestrial hospitals. Commercial air eliminating filters are not designed for the high pressure-driven flow rate that may be necessary during resuscitation, or that may be necessary to advance fluids in microgravity and are unable to perform air exclusion in sufficient quantities to address the higher gaseous content typically encountered in microgravity environments.

Referring now to FIG. 1, an exemplary embodiment of an inline microgravity air trap device 100 is illustrated. Device may include a body 104 which may include one or more components of microgravity air trap device 100 as introduced in further detail hereinbelow. An exemplary embodiment of an inline microgravity air trap device 100 is displayed in FIG. 1 with body 104 partially cut away to illustrate embodiments of components of microgravity air trap device 100. Body 104 may be constructed of any suitable material; material composition of body 104 may include, without limitation, any material or combination of materials suitable for use in intravenous fluid delivery and sampling systems, such as without limitation biocompatible polymers such as plastics, from metals, ceramics, or the like. Persons skilled in the art, upon reviewing the entirety of this disclosure, will be aware of various examples of materials and/or combinations thereof that may be suitable for composition of body 104 as consistent with this disclosure. Body 104 may be manufactured according to any suitable process or combination of processes including without limitation molding processes such as injection molding, blow molding, or the like, additive manufacturing processes such as, without limitation, stereolithography, selective laser sintering, powder-jet printing, fused deposition, or the like, subtractive manufacturing processes such milling or drilling on a lathe and/or end-mill machine tool, or the like; persons skilled in the art, upon reviewing the entirety of this disclosure, will be aware of various ways in which body 104 may be manufactured consistently with this disclosure. For instance, and without limitation, body 104 may be additively manufactured from a design file such as a computer assisted design (CAD) file using a nylon 12 polyamide powder on a selective laser sintering 3D printer.

Still referring to FIG. 1, microgravity air trap device 100 includes an elongate air trap chamber 108. Elongate air trap chamber 108 may be formed in body 104, for instance by means of any manufacturing process and/or combination thereof suitable for manufacture of body 104. Air trap chamber 108 includes a blind end 112, an opposite air outlet end 116 containing a gas egress opening 120, and a longitudinal axis 124 running from the blind end 112 to the air outlet end 116. In an embodiment, chamber 108 may be cylindrical, where "cylindrical" indicates that a cross-section of chamber 108 taken in a plane transverse to longitudinal axis 124 is substantially circular and/or elliptical in outline, excluding any irregularities introduced by openings from inlet and/or outlet ports 140 as described in further detail below.

Continuing to refer to FIG. 1, microgravity air trap device 100 includes a fluid inlet port 128 connecting air trap chamber 108 to a pressurized fluid supply. Connection to pressurized fluid supply may be effected via a length of IV tubing and/or one or more additional IV assembly components such as valves, y junctions, stopcocks, or the like. Pressurized fluid supply may include any source of fluid provided under a pressure exceeding ambient pressure outside of an IV assembly incorporating microgravity air trap device 100, such as an air pressure in a spaceship, space flight vehicle, space flight capsule, or space station, or local air pressure where microgravity air trap device 100 is being used in a terrestrial setting. Pressurized fluid supply may be received from a pressure source (not shown) connected to fluid inlet port 128 via IV tubing or the like, including without limitation exemplary pressure sources as described in further detail below. Fluid inlet port 128 may include a connector 132 formed for fluidic connection to an intravenous line, where "fluidic connection" and "connection," as used herein, indicate connection of internal spaces and/or lumens 212 via openings permitting fluid to flow from one element to another; as a non-limiting example, fluid inlet port 128 opens into chamber 108 so that fluid contents of an IV tube or other component connected to fluid inlet port 128 will empty into chamber 108 when urged through such IV tube and/or component by pressure or other forces. Connector may include, without limitation, an IV connector such as a split septum connector, mechanical valve connector, or other connector or port designed to be inserted into IV tubing. Connector may include without limitation a male or female Luer lock. Fluid inlet port 128 may include at least a grip projection 136 extending from the surface of the fluid inlet port 128. At least a grip projection 136 may include any projection that makes fluid inlet port 128 easier for a user to grasp, including without limitation a ridge and/or two ridges opposite each other across a longitudinal axis 124 of the inlet port 128, or the like. In an embodiment, fluid inlet port 128 may be disposed between blind end 112 and air outlet end 116. Fluid inlet port 128 may be attached to, incorporated in, and/or manufactured as a monolithic whole with body 104.

Still referring to FIG. 1, microgravity air trap device 100 includes a fluid outlet port 140 connected to a fluid delivery destination. Connection may be effected via a length of IV tubing and/or one or more additional IV assembly components such as valves, y junctions, stopcocks, or the like. Fluid delivery destination may include a device configured for delivery of fluid to a blood vessel of a patient; such a device may include without limitation a syringe, a catheter, a cannula, and/or any other device suitable for delivery of fluid into or extraction of fluid from a blood vessel via an IV assembly. Fluid outlet port 140 may include a connector 140 formed for fluidic connection to an intravenous line; connector 140 may include any connector suitable for use as a connector 132 as described above. Fluid outlet port 140 further may include at least a grip projection extending from the surface of the fluid outlet port 140; at least a grip projection may include any component suitable for use as at least a grip projection 136 as described above. Fluid outlet port 140 may be disposed between blind end 112 and air outlet end 116. In an embodiment, chamber 108 has no openings apart from an opening connecting chamber 108 to inlet port 128, an opening connecting chamber 108 to outlet port 140, and gas egress opening 120; for instance, blind end 112 may have no openings, and interior walls of chamber 108, aside from those three openings, may have no openings.

With continued reference to FIG. 1, microgravity air trap device 100 includes a filter 148 forming a filter 148 tube having an interior containing longitudinal axis 124, the filter 148 tube having a first tube end 152 at the blind end 112 of the air trap chamber 108 and a second tube end 156 at the gas egress opening 120. Filter 148 may include any filter 148 suitable for exclusion of water from gas; for instance, and without limitation, filter 148 may include a membrane filter 148. Membrane filtration, as used herein, is physicochemical separation process that employs thin, primarily synthetic polymeric, semi-permeable membranes to separate intermixed substances from one another. Filter 148 and/or a membrane filter may be constructed out of any one or combination of a wide range of synthetic materials, including without limitation cellulose acetate, cellulose nitrate (collodion), polyamide (nylon), polycarbonate, polypropylene, and polytetrafluoroethylene. Materials making up a membrane filter may form a complex network of fine, interconnected channels; alternatively, a filter material such as a polycarbonate filter may include cylindrical pores of uniform diameter that pass directly through the filter 148. In either case, filter 148 may be described as having a "pore size" representing an average minimum passage diameter for a passage through which materials may pass through filter 148. Pore size may be selected to accept gas exchange with maximal efficiency under pressures in use in microgravity air trap device 100. As a non-limiting example, filter 148 may have a pore size of between 100 and 200 micrometers.

In an embodiment, and still referring to FIG. 1, filter 148 may include a hydrophobic membrane filter. A hydrophobic membrane filter, as used herein, is a filter in which electrostatic attraction between a material making up the filter 148 and water molecules is less than an electrostatic attraction between water molecules and other water molecules; this is in contrast to a hydrophilic filter, where the electrostatic attraction between the water molecules and the material is greater than the attraction between the water molecules themselves, and/or a neutral filter where the electrostatic attraction between the water molecules and the material is approximately the same as the attraction between the water molecules themselves. A hydrophobic filter material may have a contact angle, with a water drop placed thereon, of greater than 90°. A hydrophobic filter may act to repel water; in an embodiment, where filter 148 is hydrophobic, filter 148 may act to exclude water and/or fluids from an interior of filter 148 tube while allowing air or other gasses to pass through into the interior of the filter 148 tube. A hydrophobic filter may be constructed from any suitable materials, including without limitation polypropylene and/or polytetrafluoroethylene (PTFE).

With continued reference to FIG. 1, microgravity air trap device 100 structural insert 160 in the interior of the tube. Structural insert 160 may be constructed of any material or combination of materials suitable for use in construction of body 104. Structural insert 160 may be constructed using any method or combination of methods suitable for construction of body 104. Structural insert 160 may be constructed in the same process used to construct body 104, and/or as an integral part of body 104; alternatively or additionally, structural insert 160 may be inserted into chamber 108 and attached to body 104 to assemble device, for instance as described in further detail below. Structural insert 160 may be inserted into and/or attached to filter 148 tube prior to insertion in chamber 108. Structural insert 160 may be constructed in the same manufacturing process as filter 148; for instance and without limitation, both structural insert 160 and filter 148 may be created together in an additive manufacturing process. Materials used in a joint additive manufacturing process may have qualities and/or attributes desired in filter; for instance, filter 148 and structural insert 160 may be manufactured in a selective laser sintering, binder-jet, fused deposition, stereolithographic, or other additive process using polymer materials, where the polymer materials used are hydrophobic. Manufacturing structural insert 160 and filter 148 tube together may have the effect that filter 148 tube is affixed to one or more parts of structural insert 169 such as ribs of structural insert 160 and/or one or both ends of structural insert 160, as described in further detail below. In an embodiment, structural insert 160 is formed to support filter 148 tube and/or to guide air and/or gasses extracted through filter 148 to gas egress opening 120, for instance as set forth in further detail below.

Figure 2:
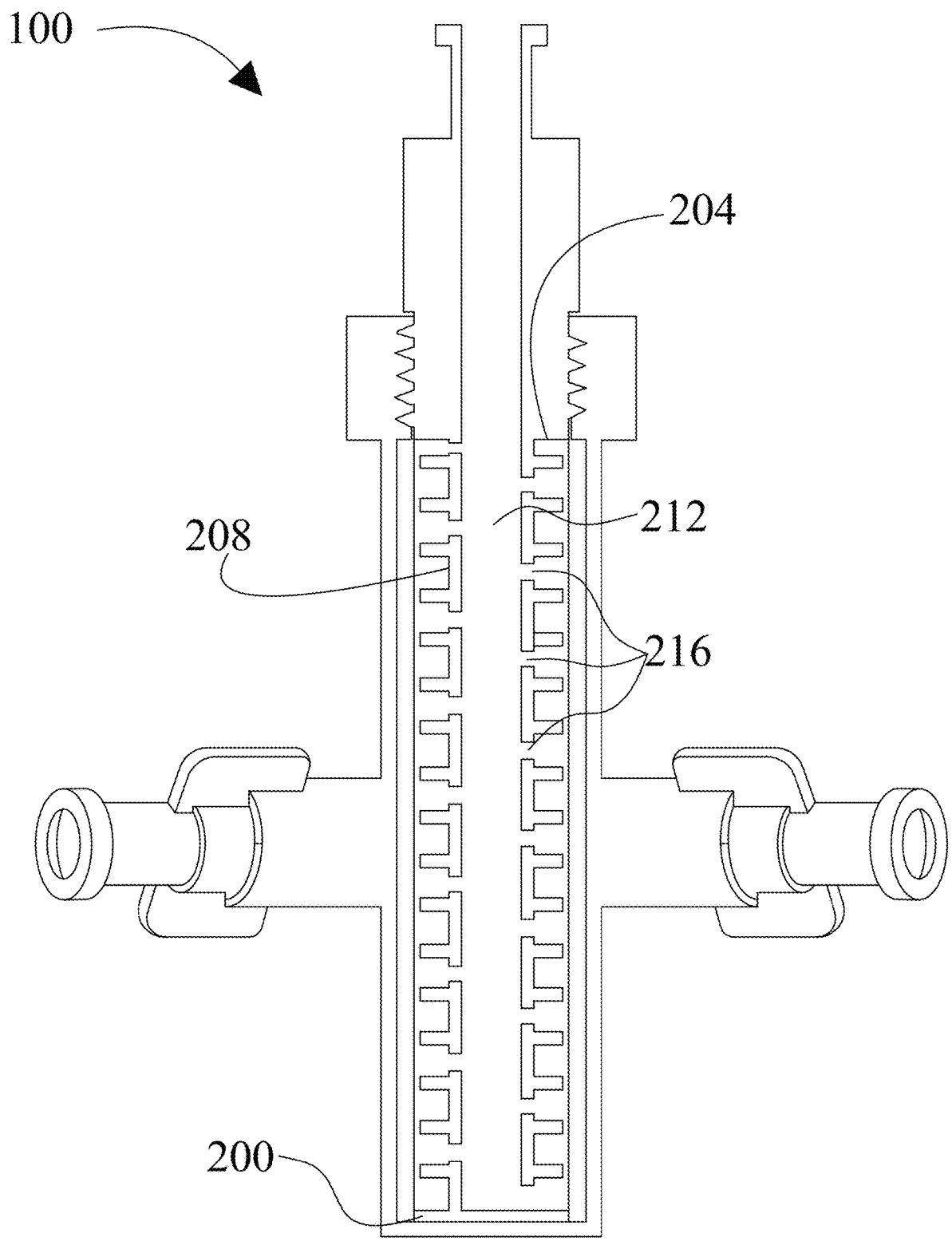
FIG. 2 is a schematic diagram illustrating an exemplary embodiment of a microgravity air trap device.

Referring now to FIG. 2, an exemplary embodiment of microgravity air trap device 100 is illustrated with a cross-sectional view of chamber 108, filter 148, and structural insert 160. Structural insert 160 includes a first insert end 200 located at first tube end 152 and blind end 112. First insert end 200 may be pressed and/or sealed against blind end 112. Structural insert 160 includes a second insert end 204 located at second tube end 156 and air outlet end 116. First tube end 152 may be affixed and/or sealed to first insert end 200 and/or gas egress opening 120, where affixing and/or sealing may be performed using any suitable method, including without limitation heat sealing, adhesion, or the like. Second tube end 156 may be affixed and/or sealed to second insert end 204 and/or blind end 112 using any suitable method, including without limitation heat sealing, adhesion, or the like; in an embodiment, securing end of filter 148 tube to ends of structural insert 160 and/or chamber 108 may ensure that no material passes into interior of filter 148 tube without passing through filter 148, permitting filter 148 properties such as pore size and/or hydrophobic material to take maximal effect. Where filter tube 148 and structural insert 160 are manufactured together, first tube end 152 and/or second tube end 156 may be affixed to first insert end 200 and/or second insert end 204 respectively, as part of the manufacturing process.

In an embodiment, and still referring to FIG. 2, structural insert 160 may include a hollow support tube including an exterior surface, an interior lumen 212 containing the longitudinal axis 124 and at least an opening connecting the interior lumen 212 to the exterior surface. In an embodiment, at least an opening may include one or more transverse openings 216 in structural insert 160. One or more transverse openings 216 may include a plurality of openings spaced along exterior surface; one or more transverse openings 216 may allow entry into lumen 212 of gases that have passed through filter 148, permitting such gasses to pass through lumen 212 under the influence of air pressure induced by urging of gasses through filter 148 via centrifugal force and thence toward gas egress opening 120, and/or negative pressure applied at gas egress opening 120, for instance as described below. Structural insert 160 and/or chamber 108 may be formed so that fluids and/or gasses are unable to pass through first insert end 200; in an embodiment, first insert end 200 may have no opening; in other words, first insert end 200 may be blind. Alternatively or additionally, blind end 112 may include a central convex feature shaped to seal shut an opening of the first support end when the first support end is pressed against the blind end 112; convex feature may, for instance, act as a plug to an opening at first support end.

Figure 3:
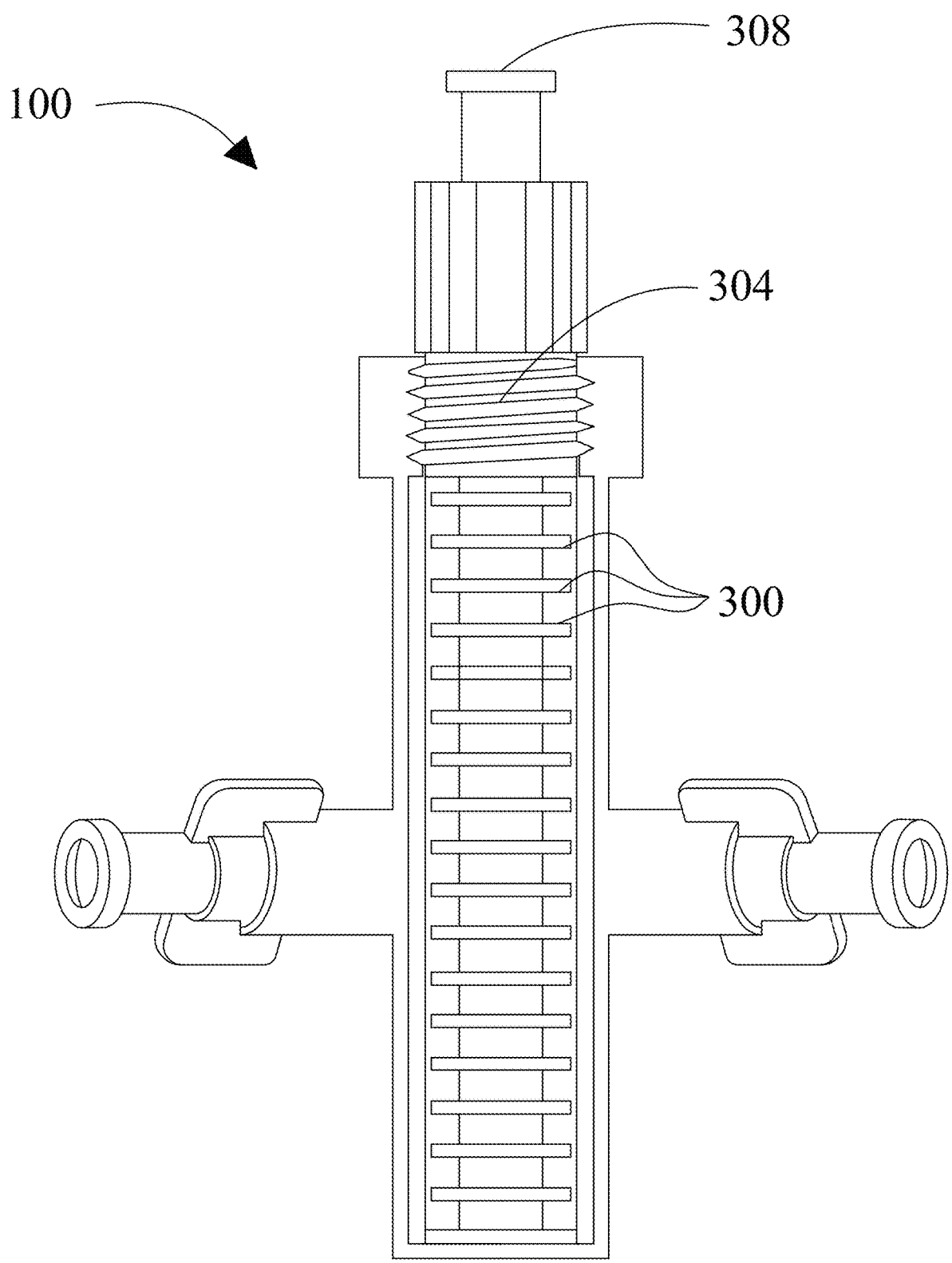
FIG. 3 is a schematic diagram illustrating an exemplary embodiment of a microgravity air trap device.

Referring now to FIG. 3, an exemplary embodiment of microgravity air trap device 100 is illustrated with a cross-sectional view of chamber 108, and filter 148, and showing an exterior surface of an embodiment of structural insert 160. In an embodiment, hollow support tube and/or structural insert 160 may include a plurality of transverse ribs projecting from the exterior surface orthogonally to the longitudinal axis 124, the plurality of transverse ribs supporting the filter 148 tube. Plurality of transverse ribs may act to hold filter 148 tube away from hollow tube, so that gasses are free to pass through more surface area of filter 148 tube than would be possible if filter 148 were pressed against exterior surface, thereby limiting gas flow to act through only the areas provided by the transverse openings 216, for instance by application of high enough pressures and/or centrifugal accelerations to overcome shear resistance and/or mechanical strength of the filter 148 material. The additional unobstructed surface area of filter 148 preserved by the presence of transverse ribs may in turn produce the advantageous effect of permitting greater quantities of gas to pass through filter 148 per unit of time. In an embodiment, greater rates of gas flow thus enabled will permit microgravity air trap device 100 to separate greater volumes of gas and/or air from fluids, enabling extraction through filter 148 to operate at high flow rates associated with higher pressure at fluid inlet port 128, the resulting higher fluid velocity and centripetal acceleration due to the curved flow path and the resulting increase in buoyant force moving bubbles towards the filter 148. Plurality of transverse ribs may have any suitable form, including rings or discs around a cylindrical hollow tube of structural insert, or any polygonal shape, curved shape, and or combination thereof desired. Rings may have gaps in rings, such that a channel through rings exists for passage of gas; alternatively no gaps may exist between rings, and gas may be constrained to enter lumen 212. Filter 148 may be affixed to ribs, for instance by adhesion or during a process of manufacturing filter 148 and structural insert 160 together.

Still referring to FIG. 3, in an embodiment, microgravity air trap 100 may include a plug affixed to second insert end 204. Plug may be formed of any material and/or combination of material suitable for use in constructing body 104 and/or structural insert 160. Plug may be attached to second end using any suitable means of attachment, including fastening with fasteners, heat sealing, and/or adhesion; plug may be formed with structural insert 160 in the same manufacturing process, forming a monolithic whole. In other words, plug may be a portion of second insert end 204. In an embodiment, gas egress opening 120 may include interior threading, and plug may further include a threaded plug 304 affixed to second insert end 204, the threaded plug 304 having exterior threading that secures the threaded plug to the interior threading; assembly of microgravity air trap 100 may include insertion of structural insert 160 into filter 148 tube, insertion of the combined structural insert 160 and filter 148 into chamber 108, rotation to engage exterior threading to interior threading, and tightening to the point of forming a seal. Plug may include a plug opening communicating and/or connected to the interior of the tube. Air and/or gasses that pass through filter 148 may travel along lumen 212 as described above and exit lumen 212 via plug opening. Trap 100 may, in other embodiments, include an air egress opening at each end of chamber, and/or plug opening at both ends; filter 148 may act to exclude fluid from openings.

Figure 4:
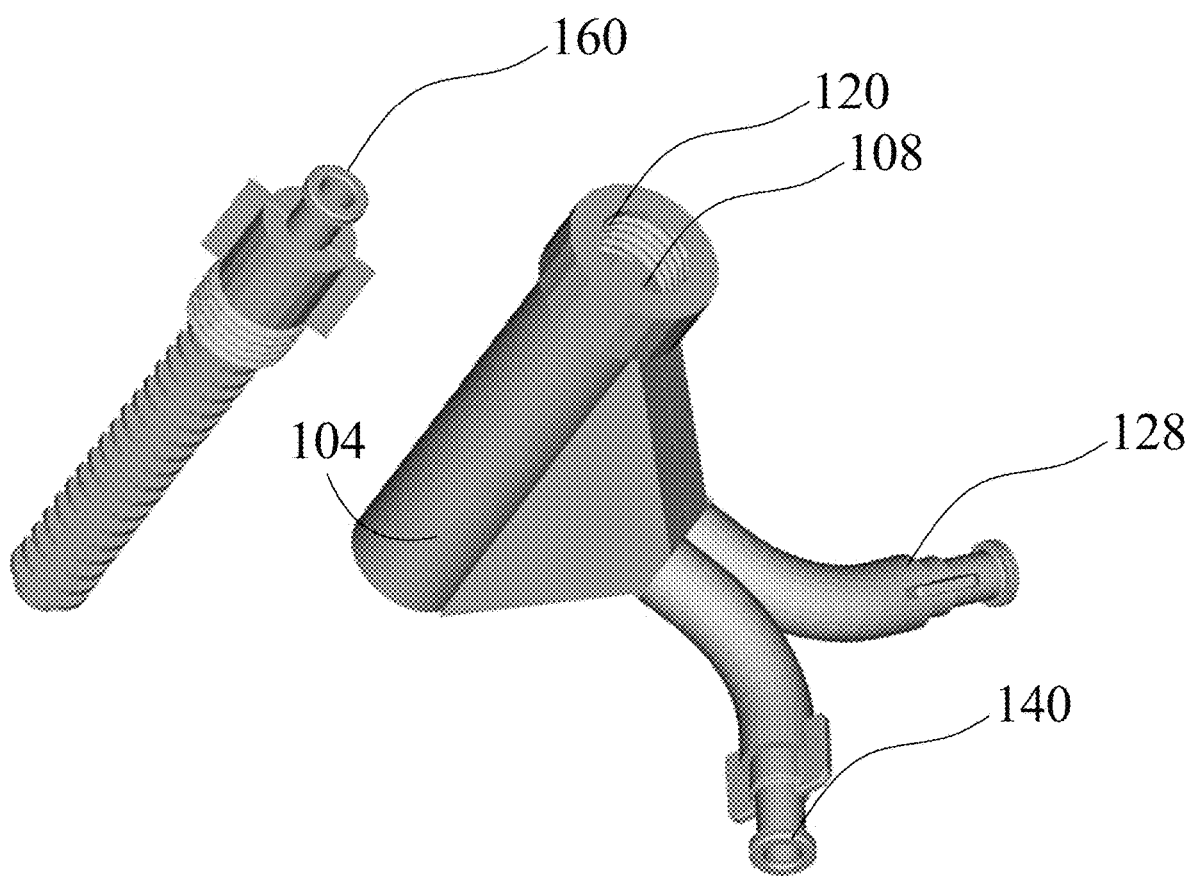
FIG. 4 is a schematic diagram illustrating an exemplary embodiment of a microgravity air trap device.

Referring now to FIG. 4, a perspective view of and exemplary embodiment body 104 showing gas egress opening 120 and a portion of chamber 108 interior, and an exemplary embodiment of insert located beside body 104, showing exterior threading of plug and plug opening, is provided for illustrative purposes. As depicted for instance in FIG. 4, plug may include at least a plug grip projection, which may include any element suitable for use as a grip projection 136 as described above. Plug may include a plug connector, which many connect to additional elements such as without limitation IV tubes and/or tubes connected to a negative pressure source as described in further detail below. Fluid inlet port 128 and/or fluid outlet port 140 may include tubal extensions from body 104. Fluid inlet port 128 and/or fluid outlet port 140 may be connected to body 104 via a connecting structure through which passages from fluid inlet port 128 and/or fluid outlet port 140 may pass into chamber 108.

Figure 5:
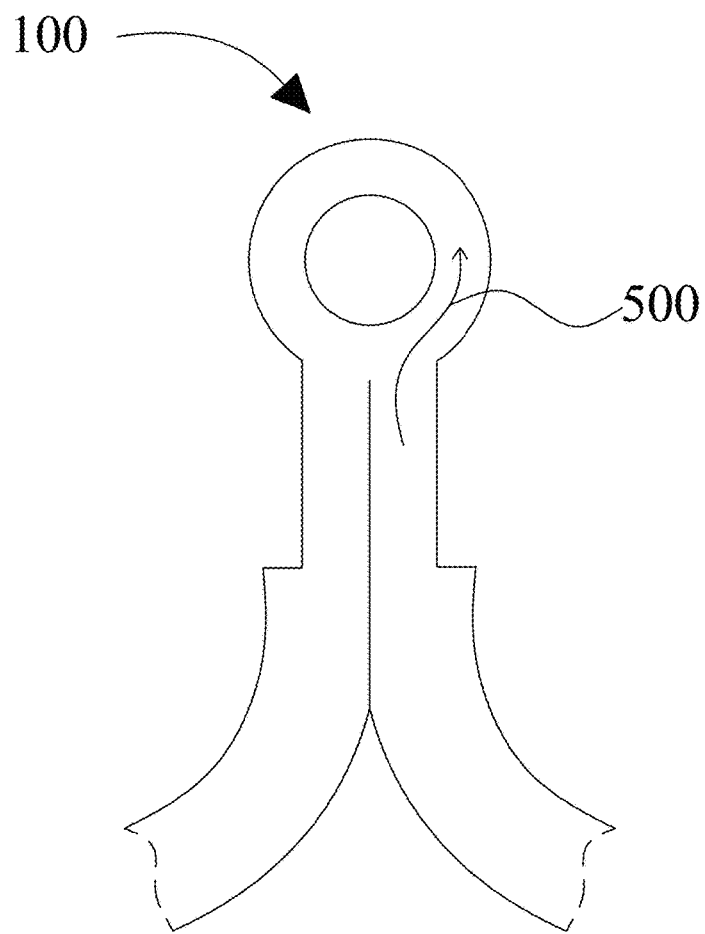
FIG. 5 is a schematic diagram illustrating an exemplary embodiment of a microgravity air trap device.

In operation, and as illustrated for instance in FIG. 5, illustrating a top sectional view of an exemplary embodiment of microgravity air trap 100, chamber 108 is formed to direct fluid from the pressurized fluid supply to accelerate in a rotational path around the filter 148, as illustrated for instance by directional arrow depicted in FIG. 5, forcing gas contained in the fluid to pass through the filter 148 into the interior of the tube. Gas-depleted fluid may then exit through outlet port 140 and into an IV tube which may connect via a catheter or syringe to a blood vessel of a patient, while gasses extracted through filter 148 via centrifugal forces may exit through gas egress opening 120 and/or plug opening. Chamber 108 may direct fluid into a curved path by virtue of a cylindrical shape of chamber 108.

Figure 6:
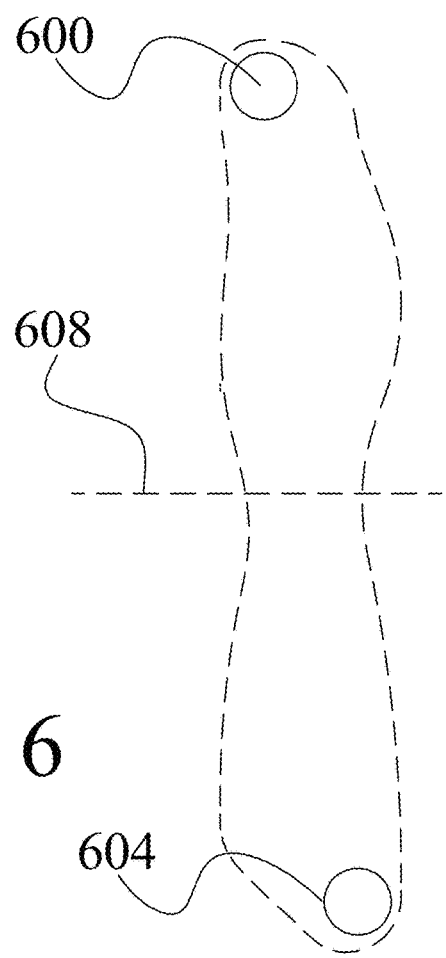
FIG. 6 is a schematic diagram illustrating an exemplary embodiment of detail of a microgravity air trap device.

Referring now to FIG. 6, a cutaway view of an embodiment of an internal wall of microgravity air trap 100 chamber 108 is illustrated. Chamber 108 may include an inlet opening 600 connected to fluid inlet port 128. Chamber 108 may include an outlet opening 604 connected to the fluid outlet port 140. Inlet opening may be formed to direct pressurized fluid toward a curved path around the longitudinal axis 124; for instance, inlet opening may be directed in a tangential direction with respect to internal wall, so that pressurized fluid initially travels in a tangential direction around the wall and away from outlet opening, so that fluid will follow a rotational path at least partway around chamber 108 prior to exiting via outlet opening 604. Fluid may not make a complete rotation around chamber 108 in some embodiments. In an embodiment, the two openings may be disposed at opposing ends of chamber 108, causing fluid to travel a long path axially prior to exiting, with the result that liquid may perform more revolutions prior to exiting, causing further gas to escape during traversal. For instance, and without limitation inlet opening may be disposed adjacent to a first end of the blind end 112 and the air outlet end 116, while the outlet opening is disposed adjacent to a second end of the blind end 112 and the air outlet end 116, where the second end is distinct from the first end. In an embodiment, an opening is disposed near to an end of the chamber 108 where opening is between that end and a midline 608 intersecting longitudinal axis 124 and equidistant from blind end 112 and air outlet end 116. Alternatively or additionally, fluid may follow a rotational and/or curved path by accelerating radially into a curved inner chamber wall, which may constrain fluid to travel in the curved path, producing the desired centrifugal and/or centripetal forces and resulting buoyancy effects as described herein. Fluid may be guided and/or forced into a rotational path using one or more redirection features (not shown) such as without limitation rifling on an interior wall of chamber, helical baffles, ledges, and/or paths for fluid to follow, and/or an initial redirection baffle at inlet opening directing fluid in a tangential or rotational direction and/or away from a radial and/or axial direction.

A prototype was tested was tested against a commercially produced Braun five micrometer air eliminating filter. A liter bag of 0.9% commercially prepared saline solution was run through IV tubing suspended at 125 cm above an embodiment of microgravity air trap. For a control, no filter was placed in the IV line. Flow rates were calculated by recording the average time to drain an IV bag. The commercial filter flow rates were recorded with one filter in line, two in parallel, and three in parallel. The filters were placed in parallel to reduce resistance in the system. An embodiment of inline microgravity air trap device was recorded in the same manner. The times were then recorded for the same configurations with the IV bag pressurized to 150 PSI and 300 PSI via a pressure bag. Air elimination ability was recorded by injecting 60 ml of air into the flowing IV line via a three-way stopcock and syringe. The experiments were again repeated using one Braun filter in line, two in parallel, three in parallel, and finally an embodiment of inline microgravity air trap device 100. A one-way valve was also placed in the line just distal to the IV bag to eliminate air flowing back up into the bag. First the air bolus was injected slowly over 60 seconds into the line pre-filter to simulate numerous small bubbles. The air entrained in the closed collection bag downstream of the filters was then measured. The slow air bolus was conducted with pressures induced by gravity by suspension of bag 125 cm H$_2$O over microgravity air trap 100, 150 PSI, and 300 PSI. All filters were properly primed. The experiment was then repeated using a fast air bolus: 60 ml of air injected over 5 seconds to simulate a large pocket of air entering the filter. Again, all four filter configurations were tested at pressures of 125 cm suspension, 150 PSI, and 300 PSI.

The embodiment of inline microgravity air trap 100 behaved comparably to the commercial inline filter at low flow rates and pressure but unexpectedly performed significantly better at higher driving pressure. In addition, the embodiment of inline microgravity air trap device 100 outperformed all configurations of the commercial filters at fast air boluses, indicating superior performance in management of larger air volumes intermixed with fluids. Interestingly, performance improved as flow rate increased, likely caused by the increased centrifugal force within the chamber 108.

Figure 7:
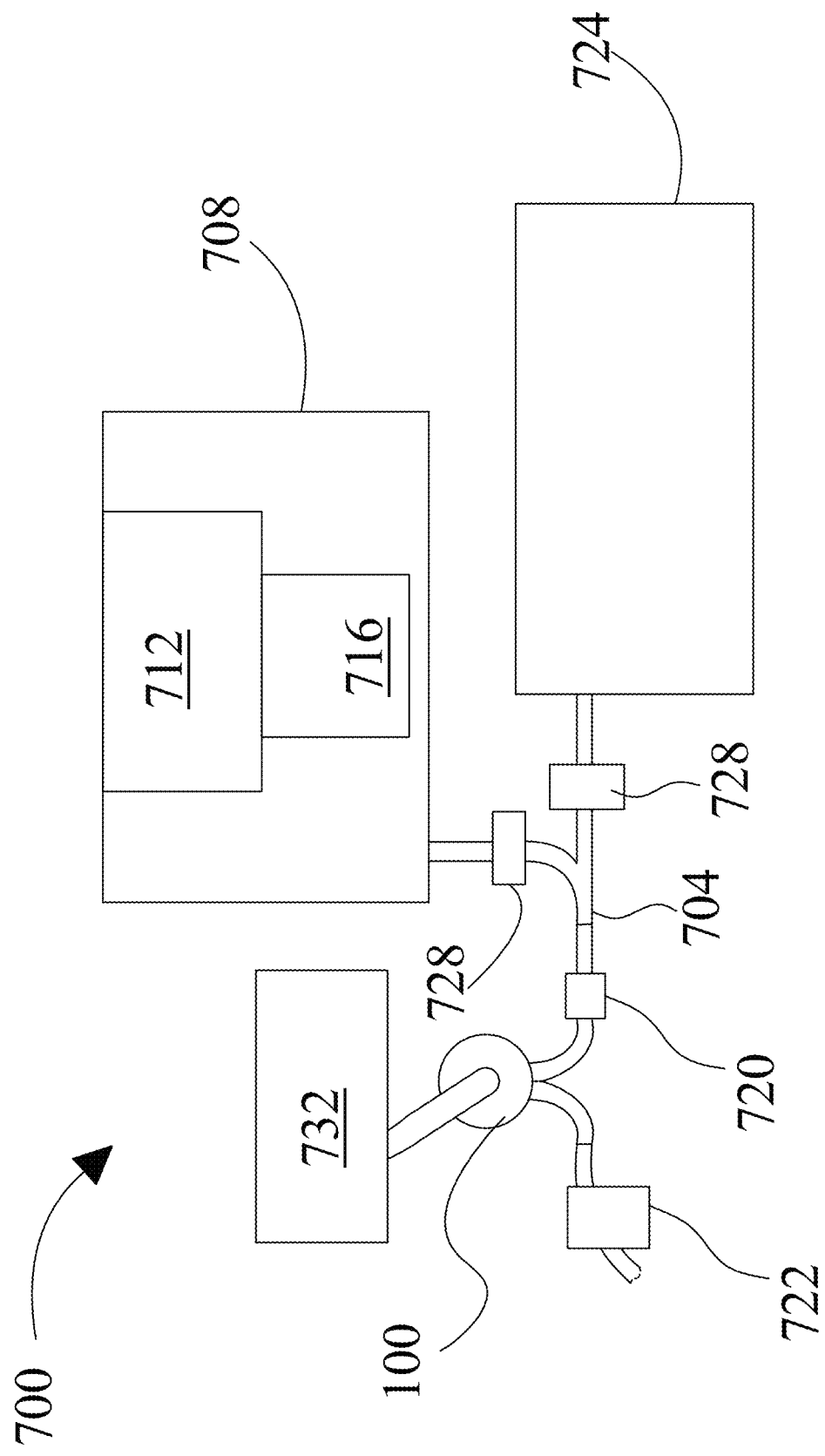
FIG. 7 is a block diagram illustrating an exemplary embodiment of an IV assembly.

Referring now to FIG. 7, an exemplary embodiment of an intravenous fluid delivery assembly 700 incorporating an inline microgravity air trap device. In an embodiment, the intravenous fluid delivery assembly includes a microgravity air trap device 100, which may include any microgravity air trap device 100 as described above in reference to FIGS. 1-6. Assembly may include an incoming fluid line 704 connected to a fluid inlet port 128 of microgravity air trap device 100 and to a first pressure source 708. First pressure source 708 may include a pressurized container of fluid, such as a pressure bag; pressurized container may be pressurized by pumping air into the container, which may include sterile air, using for instance a pumping syringe or electric air pump. Pressurized container may be pressurized by application of pressure by an external source around container; for instance, pressurized container may include an IV bag with a blood-pressure cuff placed around the bag and activated to exert pressure on the bag. Pressure may be exerted by squeezing manually, or any other source of external pressure. First pressure source may include a positive pressure source that forces fluid through air trap device 100. Alternatively or additionally, first pressure source may exert negative pressure to draw fluid through air trap device 100.

Alternatively or additionally, and still referring to FIG. 7, first pressure source 708 may include a pump. Pump may include, without limitation, any form of infusion pump. For instance, and without limitation, pump may include a peristaltic pump driven by an electric or pneumatic motor, where a peristaltic pump is a pump in which liquid to be pumped is contained in a flexible tube disposed within a pump casing, and one or more rollers external to the tube compress the tube in a direction of intended liquid flow, forcing liquid through the tube in that direction. Persons skilled in the art, upon reviewing the entirety of this disclosure, will be aware of various examples of peristaltic pumps that may be used consistently with this disclosure. A pump may include an impeller driven by an electric motor; impeller may include a magnetically driven impeller disposed within a container and/or tube containing liquid, the impeller having one or more permanent magnets that cause the impeller to rotate under the influence of corresponding magnets and/or changing magnetic fields exterior to the container and/or tube.

With continued reference to FIG. 7, pump may include a control circuit 712, the control circuit 712 configured to regulate a pressure of the pressurized fluid. Control circuit 712 may include any electronic circuit that may be configured as described below; for instance, control circuit 712 may include a logic circuit incorporating one or more logic gates. Control circuit 712 may include a microprocessor, microcontroller, or any computing device as described in further detail elsewhere in this disclosure. Control circuit 712 may be connected to a power source such as a generator, battery, electrical outlet, or the like; power source may include backup and/or uninterruptible power sources to maintain control circuit 712. Control circuit 712 may be configured to drive a pump to achieve a target pressure; target pressure may be set by calibrating voltage and/or current from an electrical power source to pressure levels, such that increasing voltage and/or current by a set amount results in a set amount of pressure increase in pump output. Alternatively or additionally, control circuit 712 may be connected to a pressure sensor 716 that detects fluid pressure within assembly 700. In an embodiment, a user and/or a programmed set of instructions indicate a target pressure to control circuit 712, and control circuit 712 drives pump to increase pressure until target pressure is achieved; control circuit 712 may use pressure feedback to maintain a target pressure within some tolerance by repeatedly sampling pressure within assembly 700 and adjusting pump speed to increase or decrease pressure as needed to achieve target pressure.

Continuing to refer to FIG. 7, a user and/or set of programmed instructions may set pressure according to one or more operational parameters. For instance, and without limitation, pressure may be set higher where external gravity is lower, to counteract greater degrees of gas intermixing attendant to lower gravity environments as described above; as a non-limiting example, a first default pressure level may be set in microgravity environments, a second, lower, default pressure level may be set in environments that are lower than Earth-surface gravity but higher than microgravity, such as levels that may be experienced on a moon or asteroid, or induced using centrifugal force in a rotating spacecraft, and a third default level, lower than the first level and the second level, set in environment having Earth-surface gravity levels. Default levels may be multiplied by factors based on other parameters affecting desirable pressure levels or may be used as factors multiplied by pressure levels set according to such parameters. An additional factor may include a type of blood vessel into which an IV is being inserted; where the blood vessel is an artery, for instance, a higher default pressure level and/or factor may be used to increase pressure in assembly, because of lower air bubble tolerance in arterial vessels. Where blood vessel is a vein, default pressure and/or a factor may be set lower reflecting a lower needed pressure due to a relatively high tolerance of bubble inclusion in veins. A factor and/or default pressure may be set according to whether the IV is a central line, requiring more pressure according to Poiseuille's law, or a peripheral line. A factor and/or default pressure level may be set based on proximity to readily damaged anatomy such as a brain, indicating a higher desired pressure to produce a lower proportion of bubbles, or to mitigating anatomy such as lungs, indicative of a lower needed pressure due to ability of lungs to dissipate gas bubbles; "proximity" in this context may indicate shortness of a circulatory path to the anatomical feature in question. A factor may be set according to a proportion of gas in a fluid; for instance, a higher factor may be set for a fluid reservoir having a greater proportion of air, while a lower factor may be set for a fluid reservoir known to have a lower proportion of air. A factor and/or default pressure level may be set according patient condition; for instance, a pressure level may have an upper bound representing a maximal pressure that a patient can tolerate, and a minimal pressure based on a degree of air bubble inclusion the patient can tolerate.

Still referring to FIG. 7, control circuit 712 may be configured to derive target pressure by aggregating factors and/or default pressure levels, for instance as determined above. Aggregating may include multiplying factors and/or default pressure levels together, averaging factors and/or default pressure levels, for instance by calculating an arithmetic mean, or the like to get a pressure level to be applied. Alternatively or additionally, parameter values, default pressure levels, and/or factors may be used to query a data structure such as a database table or the like listing target pressures associated with different sets of parameters, factors, and/or default pressure levels. Factors may be manually entered by users or preprogrammed based on default assumptions. Users may be prompted via graphical user interfaces having fields and/or checkmarks corresponding to each parameter where a user may set parameter levels, factors, and/or default pressure levels according to observations and/or predictions regarding such parameters.

Still referring to FIG. 7, in an embodiment, control circuit 712 may be configured to detect blockage in assembly; this may be accomplished, for instance, by storing a threshold pressure level in memory of control circuit 712 and sensing, using pressure sensor 716, a pressure level in excess of the threshold pressure level. Control circuit 712 may switch off pressure in response to blockage detection. Control circuit 712 may emit an alarm based on the detected blockage. Control circuit 712 may be configured to detect a leak in assembly; this may be accomplished, for instance, by storing a threshold pressure level in memory of control circuit 712 and sensing, using pressure sensor 716, a pressure level less than the threshold pressure level. Control circuit 712 may switch off pressure in response to leakage detection. Control circuit 712 may emit an alarm based on the detected leak.

With continued reference to FIG. 7, control circuit 712 may be configured to provide a continuous or near continuous infusion via the assembly. Control circuit 712 may provide the infusion by determining an amount per unit of time of fluid to be delivered. Control circuit 712 may then determine an amount of fluid per unit of time delivered at the target pressure; control circuit 712 may generate a duty cycle in which a proportion of a unit of time sufficient to deliver the fluid to be provided in that unit of time at the target infusion rate would be provided at the target pressure is set as a time during which to pump at the target pressure, and the remainder of time in the unit of time is spent at zero pressure. Unit of time may be any suitable unit, including without limitation a second, a minute, a number of clock cycles of a reference clock in control circuit 712, or the like. Infusion may then be delivered in a series of pulses at target pressure, separated by pauses of sufficient length to achieve a target infusion rate.

With continued reference to FIG. 7, assembly may include a pressure-activated valve 720 that opens only upon a pulse exceeding a certain pressure; for instance, a biasing means may hold the valve closed unless pressure exceeds a threshold amount, such as a minimal driving pressure for fluid administration. Pressure-activated valve 720 may be placed, as a non-limiting example, immediately before fluid inlet port 128; pressure-activate valve may act to exclude air bubbles that may diffuse through fluid and through microgravity air trap during cessation of liquid delivery in a pulse cycle, between boluses, or the like.

Alternatively or additionally, gradual infusions may be performed by emptying outflow from microgravity air trap 100 into a secondary reservoir 722. Secondary reservoir may, without limitation, be initially emptied of all contents by pulling vacuum or the like, ensuring that or almost no gas is initially present; any alternative method for ensuring that secondary reservoir is empty of gasses may be employed. In an embodiment, fluid may be pushed through trap 100 at an optimal pressure for gas exclusion, and gas-free or depleted fluid may be collected in secondary reservoir, to be dispensed at a different pressure and/or rate to patient; any pressure source and/or technique may be used to dispense fluid from secondary reservoir 722. One or more valves in the line between trap 100 and secondary reservoir may prevent later bubble osmosis or drift into secondary reservoir, including a pressure-activated valve as described above, a check-valve, and/or a manually activated valve.

Still referring to FIG. 7, assembly may include a second pressure source 724. Second pressure source 724 may include any pressure source suitable for use as first pressure source 708. Second pressure source 724 may act as secondary IV and/or "piggyback" IV, which may be used to administer an IV medication in a bolus or smaller dose than first pressure source 708; second pressure source 724 may be joined to assembly, using, for instance, a Y-junction, prior to microgravity air trap 100; alternatively each pressure source may run through its own microgravity air trap. In an embodiment second pressure source 724 is set at a lower pressure than first pressure source 708; alternatively or additionally, IV assembly may include one or more checkvalves 728 to prevent backup, which may function to prevent backups even in pulsed infusion methods as described above. Assembly may include one or more insertion points for administration of medication via syringe or plunger, for instance including one or more Y-junctions with cock-valves or the like.

With continued reference to FIG. 7, assembly includes an outgoing fluid line connected to fluid outlet port 140 of microgravity air filter 148. Outgoing fluid line may connect to one or more devices configured for insertion into a blood vessel, including without limitation a cannula, catheter, or other device for insertion in a blood vessel of a patient. A clamp and/or other pressure throttling regulator may be connected to outgoing fluid line.

Still referring to FIG. 7, assembly may include a negative pressure source 732 at air-egress opening; negative pressure source may be connected to plug opening and/or plug connector. Negative pressure source 732 may include any vacuum source, including without limitation a medical vacuum line, a pump intake, or the like. In an embodiment negative pressure source 732 may act to draw away air and/or gas extracted from fluid by microgravity air trap 100 as described above.

Referring now to FIG. 8, a partially cut away view of an alternative exemplary embodiment 800 of a microgravity air trap is illustrated. Microgravity air trap includes a body 804, which may be implemented in any manner and using any material suitable for body 104 as described above. Microgravity air trap includes an air trap chamber 808, which may be implemented according to any means and/or method for implementation of air trap chamber 108 as described above; air trap chamber 808 have a first end 812 and a second end 816. Either or both ends may include a gas egress opening 820, which may be implemented in any way suitable for implementation of air egress opening 120 as described above; in other words, gas egress opening 820 is connected to at least one of the first end and the second end. Microgravity air trap 800 includes a fluid inlet port 824 at first end 812 and a fluid outlet port 828 at second end. Either of fluid inlet port 824 and/or fluid outlet port 828 may include and/or be included in any connector as described above.

Still referring to FIG. 8, microgravity air trap 800 may include a structural insert 832, which may be implemented and/or manufactured in any manner suitable for a structural insert 160 as described above. A filter tube (not shown) may be supported by structural insert and inserted in chamber 808 in any manner as disclosed above. Insert may include one or more transverse ribs 836, which may be implemented as described above; insert may include transverse openings (not shown) which may be implemented as described above.

With continued reference to FIG. 8, microgravity air trap 800 may include a helical baffle 840. Helical baffle 840 may include a chamber portion 844 attached to interior walls of chamber 808, and an insert portion 848 attached to insert; filter tube may fit into a gap between chamber portion 844 and insert portion 848. Where an elastic membrane as described below is used, fluid at low pressure may travel around insert portion 848 of baffle 840, while fluid pressure at higher pressures may force elastic membrane away from a longitudinal axis, for instance as described above, and chamber portion 844 may add to a helical path of fluid. In an embodiment, helical baffle 840 may force fluid passing from fluid inlet port 824 to fluid outlet port 828 to follow a helical path imposing angular momentum on fluid and forcing fluid to rotate two or more times about longitudinal axis prior to exiting fluid outlet port 828; this may help to guarantee removal of air or other gases across filter, into filter tube, and out air egress opening or openings 820.

Referring now to FIG. 9, a cross-sectional view of first end 812 of microgravity air trap 800 is illustrated. In an embodiment, fluid inlet port 824 may be connected to a redirection shaft 900, which may force fluid entering fluid inlet port 824 into a rotational path; this may be accomplished, without limitation, by forcing and/or directing fluid onto helical baffle 840. In an embodiment, fluid inlet port may be mounted axially; in other words, longitudinal axis may pass through fluid inlet port. Where fluid inlet port is mounted axially, redirection shaft 900 may shunt fluid away from longitudinal axis, while filter tube interior 904, which may be implemented according to any embodiment described above, may be located about longitudinal axis as described above. An air egress shaft 908 may direct air from filter tube interior 904 to air egress opening 820, which may be offset to one side of longitudinal axis. Each of redirection shaft 900 and air egress shaft 908 may be formed as part of any component of microgravity air trap 800; for instance, and without limitation, each of redirection shaft 900 and air egress shaft 908 may be formed as part of structural insert 832. Filter tube 912 may be located about structural insert as described above and may function to filter out air bubbles as described above. Fluid may flow between elastic membrane and filter tube.

Referring now to FIG. 10, a cross-sectional view of second end 816 of microgravity air trap 800 is illustrated. In an embodiment, fluid outlet port 828 may be connected to a redirection shaft 1000, which may force fluid exiting fluid outlet port 828 toward fluid outlet port; this may be accomplished, without limitation, by forcing and/or directing fluid from helical baffle 840 toward fluid outlet port. In an embodiment, fluid outlet port 828 may be mounted axially; in other words, longitudinal axis may pass through fluid outlet port 828. Where fluid outlet port is mounted axially, redirection shaft 1000 may shunt fluid from rotational path to longitudinal axis at or near to second end 816, while filter tube interior 904, which may be implemented according to any embodiment described above, may be located about longitudinal axis as described above. An air egress shaft 1004 may direct air from filter tube interior 904 to air egress opening 820, which may be offset to one side of longitudinal axis. Each of redirection shaft 1000 and air egress shaft 1004 may be formed as part of any component of microgravity air trap 800; for instance, and without limitation, each of redirection shaft 1000 and air egress shaft 1004 may be formed as part of structural insert 832.

Referring now to FIG. 11, apparatus may include an elastic membrane. Elastic membrane 1100 may be formed of latex, elastic silicone, nitrile rubber, polyvinyl chloride, neoprene, isoprene, and/or any other elastic medical-safe material; "elastic," as used in this disclosure, means having sufficient elasticity to deform to fill chamber portion under fluid pressure from inlet port, where fluid pressure does not exceed a maximum medically permitted pressure for an intravenous line; permitted pressure may be a pressure between 0 and 300 mmHg (4 kPa). Elastic membrane may form a tube around structural insert. In an embodiment, as shown for instance in FIG. 12, elastic membrane 1100 may be sealed to both ends of structural insert, dividing air trap chamber into an interior section 1200 enclosing structural insert and an exterior section 1204 enclosing the chamber portion 844 of the helical baffle. Elastic membrane may have a first end 1208 sealed to first insert end of insert. Sealing may be performed in any manner for attaching filter tube to insert as described above. Inlet opening 900 may open into interior section 1200. As a result, fluid entering from inlet port may be directed around insert portion 848; where pressure increases, elastic membrane may stretch to accommodate greater fluid volume, causing fluid to traverse chamber portion 844 albeit with elastic membrane 1100 separating fluid from chamber portion 844. As shown in FIG. 13, elastic membrane may further include a second end 1300 sealed to second end of structural insert. Outlet opening may be located in the interior section.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
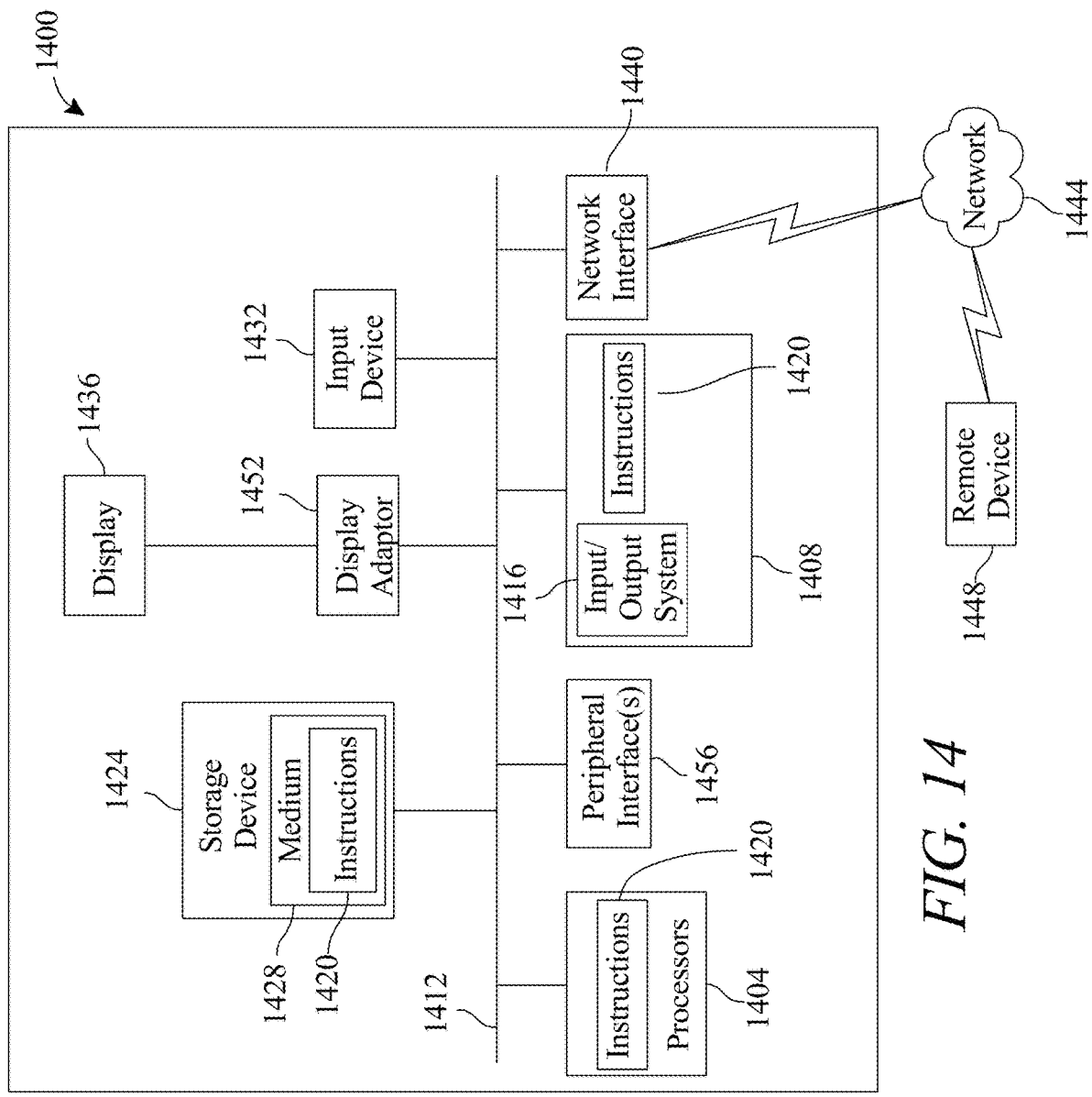
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Memory 1408 may include various components (e.g., machine-readable media) including, but not limited to, a random-access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments disclosed herein. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An inline microgravity air trap device, the device comprising:
    an elongate air trap chamber, the air trap chamber having a first end, an opposite second end, and a longitudinal axis running from the first end to the second end;
    at least a gas egress opening connected to at least one of the first end and the second end;
    a filter, the filter forming a filter tube having an interior containing the longitudinal axis, the filter tube having a first tube end at the first end and a second tube end at the second end;
    a structural insert in the interior of the filter tube, the structural insert having a first insert end located at the first tube end and a blind end, and a second insert end located at the second tube end and an air outlet end, wherein the structural insert further includes:
        a fluid inlet port located at the first insert end and connecting the air trap chamber to a pressurized fluid supply; and
        a fluid outlet port located at the second insert end and connecting the air trap chamber to a fluid delivery destination; and
    a helical baffle running from the first end to the second end;
    wherein the helical baffle is formed to direct fluid from the pressurized fluid supply to accelerate centrifugally around the filter, forcing gas contained in the fluid to pass through the filter into the interior of the filter tube.

2. The device of claim 1, wherein the chamber is cylindrical.

3. The device of claim 1, wherein:
    the structural insert further comprises an inlet opening connected to the fluid inlet port; and
    the inlet opening is formed to direct the pressurized fluid toward the helical baffle.

4. The device of claim 3, wherein the structural insert further comprises an outlet opening connected to the fluid outlet port.

5. The device of claim 1, wherein the fluid inlet port further comprises a connector formed for fluidic connection to an intravenous line.

6. The device of claim 1, wherein the fluid inlet port further comprises at least a grip projection extending from a surface of the fluid inlet port.

7. The device of claim 1, wherein the fluid outlet port further comprises a connector formed for fluidic connection to an intravenous line.

8. The device of claim 1, wherein the fluid outlet port further comprises at least a grip projection extending from a surface of the fluid outlet port.

9. The device of claim 1, wherein the filter further comprises a membrane filter.

10. The device of claim 1 wherein the filter further comprises a hydrophobic membrane filter.

11. The device of claim 1, wherein the filter has a pore size of between 100 and 200 micrometers.

12. The device of claim 1 wherein the structural insert further comprises a hollow support tube including an exterior surface an interior lumen containing the longitudinal axis and at least an opening connecting the interior lumen to the exterior surface.

13. The device of claim 2 wherein the hollow support tube further comprises a plurality of transverse ribs projecting from the exterior surface orthogonally to the longitudinal axis, the plurality of transverse ribs supporting the filter tube.

14. The device of claim 1, wherein the at least a gas egress opening further comprises a first gas egress opening at the first end and a second gas egress opening at the second end.

15. The device of claim 1, wherein the helical baffle includes a chamber portion attached to the air trap chamber and an insert portion attached to the structural insert.

16. The device of claim 15 further comprising an elastic membrane enclosing the structural insert, dividing the air trap chamber into an interior section containing the structural insert and an exterior section containing the chamber portion of the helical baffle.

17. The device of claim 16, wherein the elastic membrane has a first membrane end sealed to the first insert end and a second membrane end sealed to the second insert end.

18. The device of claim 17, wherein:
    the structural insert further comprises an inlet opening connected to the fluid inlet port; and
    the inlet opening is formed to direct the pressurized fluid into an interior section.

19. The device of claim 17, wherein:
    the structural insert further comprises an outlet opening connected to the fluid outlet port; and
    the outlet opening is located in an interior section.

20. The device of claim 1, wherein an air inlet port and the air outlet port are located along the longitudinal axis.

* * * * *